United States Patent [19]

Omer

[11] Patent Number: 5,725,859
[45] Date of Patent: Mar. 10, 1998

[54] PLANT-BASED THERAPEUTIC AGENT WITH VIRUSTATIC AND ANTIVIRAL EFFECT

[76] Inventor: Osama L.M. Omer, Stelleacker-18, 79618 Rheinfelden, Germany

[21] Appl. No.: 586,739

[22] PCT Filed: Apr. 11, 1995

[86] PCT No.: PCT/DE95/00513

§ 371 Date: Jun. 3, 1996

§ 102(e) Date: Jun. 3, 1996

[87] PCT Pub. No.: WO95/29688

PCT Pub. Date: Nov. 9, 1995

[30] Foreign Application Priority Data

May 3, 1994 [DE] Germany ............................ 44 15 539.5

[51] Int. Cl.$^6$ ............................ A01N 65/00; A61K 35/78
[52] U.S. Cl. ........................ 424/195.1; 425/404; 425/405
[58] Field of Search ............................ 424/195.1, 405, 424/404

[56] References Cited

FOREIGN PATENT DOCUMENTS 8912454  12/1989  WIPO .

*Primary Examiner*—Leon B. Lankford, Jr.
*Assistant Examiner*—Christopher R. Tate

[57] ABSTRACT

A method of treating a patient infected with DNA virus of the herpes family or DNA hepatitis B or hepatitis C viruses, or suffering from chronic allergic rhino-sino-bronchitis, by administering to the said patient a pharmaceutical composition comprising at least two of the compounds selected from the group consisting of absinthe (artemisia absinthium) resin of mastic (resin pistacia lenticus) fruit of delphinium denudatum and wherein one or more of the compounds selected from the group consisting of rose buds (flores rosae) seeds of cardamom (fructus ellettaria cardamomum, and borage flowers (flores onosma brateatum boriginaceae) are added.

4 Claims, No Drawings

PLANT-BASED THERAPEUTIC AGENT WITH VIRUSTATIC AND ANTIVIRAL EFFECT

BACKGROUND OF THE INVENTION

1. Field of the Invention

The invention concerns a plant-based pharmaceutical agent having an antiviral, anti-allergic and virustatic effect.

2. Description of the Prior Art

The herpes simplex viruses (HSV) belong to the group of DNA viruses. Of about 70 different serological sub-types six are of importance in causing disease in humans. These are:

(1) herpes simplex virus type 1 (HSV-1)
(2) herpes simplex virus type 2 (HSV-2)
(3) varicelia-zoster virus (VZV)
(4) cytomegalovirus (CMV)
(5) Epstein-Barr virus
(6) herpes virus type 6 (HSV-6)

The hallmark of this group of viruses are the frequent recurring of disease by the reactivation of the latent virus infection. The reactivation of HSV-1 virus is for example responsible for recurrent attacks of herpes labialis and stomatitis apthosa herpetica. The HSV-2 causes the recurring, disturbing genital herpes and is also brought into relation with the carcinoma of the cervix and HIV-infection. The infectious mononucleosis is only one of the infections caused by the Epstein-Barr virus. The spectrum of EBV infection stretches from a mild subclinical monosymptomatic course to the full picture of mononucleosis. This virus settles down in the cells of the liver, causing an increase in the levels of transaminases and hepatitis. Periodically occurring depressive and anxiety disorders are also brought in association with EBV-reactivation. Cytomegalovirus (CMV) has a high level of contamination (30–40% of the population). Through placenta transmission in the carrier, the CMV can cause malformation. Moreover, infection with this virus leads to fatal pneumonia, myocarditis or hepatitis in immuncompromised hosts with HIV-infection or organ transplantation. Infections caused by hepatitis B and C viruses, which too belong to the DNA-viruses, lead to chronic active hepatitis which end up frequently in liver cirrhosis and liver insufficiency. Allergic rhino-sino-bronchitis are disorders characterized by hyperreactivity of the mucous membrane with the resulting edema of the respiratory tract. It is known to-day that also here, in many cases, viral infects prolong the lowering of the allergic or the "asthmatic" threshold of the respiratory tract.

No curative treatment for these diseases is available so far. They are treated either prophylactically (e.g. immunglobulines) or, whenever possible, purely symptomatically. A chemotherapy against HSV viruses and hepatitis B and hepatitis C viruses has been so far of little success. The reason for this lies among others, in the cytotoxicity of the newly discovered antiviral substances. The antiviral substances known so far (e.g. aciclovir) exhibit their virustatic activity only in the proliferative phase and not in the latent phase thus they are unable to eradicate the virus. Moreover these therapies are very cost consuming. For example a CMV-disease in immuncompromised host with organ transplantation may cost in USA between $10,000–$50,000. Corticoids and anti-histamines offer a temporary relief against allergic rhino-sino-bronchitis. Also these medications are associated with serious, sometimes life threatening side effects. A medical invention with anti-vital and virustatic activity, which is at the same time less costly and free from risks, is therefore highly desirable.

The herbs absinthe, resin of mastic (resin pistacia lenticus, fruit of delphinium denudatum are well-known drugs. Their anti-viral and virustatic activity is unknown so far. The seeds of cardamom (fructus elettaria cardamomum), buds of roses (flores rosae) and flowers of borage (flores onosma brateatum boraginaceae are known as spices and decorative herbs. The invention describes the antiviral and virustatic and anti-allergic activity of absinthe resin of mastic and fruit of delphinium denudatum singly or in combination with rose buds, cardamom seed and flowers of borage.

In order to demonstrate the desired antiviral, virustatic and anti-allergic efficacy following herbs and their mixtures were tested:

Group 1 Absinthe

Group 2 Resin of mastic

Group 3 Fruit of delphinium denudatum

Group 4 Absinthe and resin of mastic

Group 5 Absinthe and fruit of delphinium denudatum

Group 6 Fruit of delphinium denudatum and resin of mastic

Group 7 Absinthe, resin of mastic and fruit of delphinium denudatum

Group 8 Group 7+buds of roses

Group 9 Group 7+buds of roses and cardamom seed

Group 10 Group 7+buds of roses, cardamom seed and flowers of borage.

These herbs or their mixtures were disinfected with UV light, finely ground and passed through a sieve (less than 1 mm size) and ointment was prepared in association with the usual pharmaceutical carrier substances. For oral administration they were filled in gelatin capsules so as to get a total weight of 500 mg. of capsules. In mixtures the individual plants or their parts were combined in equal parts filled in capsules and orally administered.

In order to get an idea of the antiviral activity, patients suffering from recurrent attacks of herpes labialis were treated either externally or orally with the herbs or their combinations. Herpes labialis is the most common infection caused by herpes simplex viruses. It is a typical recurring herpes disease, reactivated under various conditions (e.g. common cold, pneumonia, intensive sun-bathing, stress situations or gastrointestinal disturbances). The single efflorescence are comparative to those of herpes zoster. Without treatment the blisters dry up within 10 to 14 days. The diagnosis was made by clinical appearance, typical localization of blisters and the ulcerations. Before entering the trial informed consent of the patient was obtained. A virustatic activity was assumed when the blisters of a fresh infection of not older than 2–3 days dried up within 3–4 days, or showed distinct signs towards remission. Proof of antiviral activity was obtained when a swab from virus blisters or from the mucous membrane of the mouth did not show any virus growth on a cell medium.

It was discovered that absinthe, resin of mastic and fruit of delphinium denudatum possess a distinct antiviral virustatic activity. Neither the rose bud nor the seeds of cardamom, nor the flowers of borage possessed alone any measurable antiviral activity. They however exert a distinct synergistic effect when combined with absinthe and/or resin of mastic and/or fruit of delphinium denudatum. The mixtures of the group 7,8,9 and 10 proved to be the most balanced and optimum for the treatment of herpes infections.

The invention is illustrated with the help of following examples:

Individually dried, finely powdered and sieved herbal materials were combined to get the invented mixture A or the invented mixture B. The fine powder was filled in capsules of the size 00 so as to give the final mixture weight of 370 mg. per capsule.

INVENTED MIXTURE A

| | |
|---|---|
| absinthe | 180 mg. |
| resin of mastic | 70 mg. |
| buds of roses | 70 mg. |
| cardamom seeds | 50 mg. |
| Total weight | 370 mg. |

INVENTED MIXTURE B

| | |
|---|---|
| absinthe | 180 mg. |
| resin of mastic | 70 mg. |
| fruit of delphinium denudatum | 120 mg. |
| Total weight | 370 mg. |

Following trials were made with the invented mixture A

Trial 1

Therapeutic use of invented mixture A in the treatment of stomatitis aphthosa herpetica Stomatitis aphthosa herpetica is the most common primary infection of the HSV-1. The attack of this disease is mainly on the children, the painful ulcerations in the mouth and the mucous membranes tend to show a spontaneous remission on eighth to tenth day. The diagnosis was based on the clinical appearance, typical localization of the ulcerations, HSV-1 antigen titer (Latex-agglutination test) and the proof of HSV-1 on the swabs from mucous membrane of the mouth. Informed consent of the patient was obtained before entering the study. An antiviral activity was assumed when, in a fresh, not older than 2–3 old infection the blisters dried up within 3–4 days or showed clear signs of remission and no virus growth could be demonstrated from the swabs of the mouth after three week treatment. Ten patients with this disease were successfully treated. No side effects whatsoever were observed.

Trial 2

Therapeutic use of the invented mixture A in the treatment of genital herpes

Like the herpes labialis the genital herpes is a typical recurring disease, which likewise is widely spread. According to an estimate about 20 million Americans are suffering from it. An acute phase of this disease heals up without any specific therapy within ten to 14 days. The diagnose was based on clinical appearance, the typical localization of the ulcerations, HSV-2 antigen titer (Latex agglutination test, values above 1:4). Before entering the study an informed consent of the patient was obtained. An antiviral activity was assumed when in a fresh, not older than 2–3 old infection, the blisters dried up within 3–4 days or showed clear signs of remission and no recurrence was observed in the following 6–8 months after treatment. Eight patients were successfully treated. No adverse effects whatsoever were observed.

Trial 3

Therapeutic use of the invented mixture A in the treatment of herpes zoster

Herpes zoster is the result of the reactivation of latent varicella-zoster virus infection, often years following an earlier chickenpox infection. The typical appearance of the zoster does not cause any diagnostic problems, the rash is limited typically to one dermatome. The painful blisters heal after 10 to 14 days—sometimes the take longer. Before entering into the study an informed consent of the patient was obtained. An antiviral activity was assumed when in a fresh, not more than 2–3 days old infection, the blisters dried up or at least showed distinct tendency towards remission and patients were free of pain after 21-day treatment. Ten patients were successfully treated with the invented mixture. No side effects whatsoever were observed.

Following trials were carried out with the invented mixture B

Trial 1

Therapeutic use of the invented mixture B in the treatment of infectious mononucleosis (EBV-infection)

The infectious mononucleosis is caused by the Epstein-Barr virus which also belongs to the group of herpes viruses. This is most probably responsible for the development of Burkitt lymphoma, the nasal-pharyngeal carcinoma and recurring anxious-depressive crisis with autonomic disturbances. Fever, throat pain and severe swellings of the cervical lymph nodules are present in every case of acute mononucleosis. The blood smear of the acute mononucleosis is for diagnosis characteristic. A lymphatic monocytes with 10% atypical T-1ymphocytes is present. The proportion of T-lymphocytes can increase up to 40%. The T-lymphocytes are large cell with varying intensity of colored plasma and varying shapes of the nuclei. Of diagnostic importance are also the presence of antibodies against the capsids of the Epstein-Bart virus and Paul-Bunnel test. As diagnostic criteria of selection, the typical clinical picture, the typical appearance of the blood smear, the Paul-Bunnel test and the presence of antibodies against the capsid of the EBV were employed. Before entering into the study an informed consent by the patient was obtained. An antiviral activity was assumed when in a fresh, not more than 2–3 old infection, clear signs of remission were observed in the clinical picture and the chemical tests of the blood, and when in blood, urine or from throat swab no EBV could be isolated. Five patients were successfully treated.

Trial 2

Therapeutic use of the invented mixture B in the treatment of CMV infected patients The disease caused by CMV produces defects in lungs, liver and urogenital tract. The transmission occurs mostly through the urogenital tract. Because of high incidence of contamination through cytomegalovirus the compliment binding test solely, which persist lifelong, is of less diagnostic value. For diagnostic selection criteria compliment binding reaction, increased levels of Gama-globulins and presence of the specific IgG-CMV were employed. Acutely CMV infected patients and children were not included in the study. Informed consent was obtained before entering into the study. An antiviral activity was assumed when the pathological blood and liver values showed clear signs of remission and when no CMV was found in the blood-smear, urine or throat swab cultures. Eight patients of this group were successfully treated. Average duration of treatment was 3 months. No side effects were observed.

Trial 3

Therapeutic use of the invented mixture B in the treatment of patients with chronic active hepatitis A chronic active hepatitis is suspected in cases of active hepatic inflammation: increased levels of transaminase over six months in the absence of external noxious agents (e.g. alcohol). For the entrance into the study following selection criteria wet, met: chronically high levels of transaminases, proof of the presence of HB- and HC-antigens and a pathological electrophoresis showing high levels of gamma-globulins and total proteins and a diagnosis of chronic active hepatitis based on liver biopsy. The normalization or at least a clear trend towards normalization of gamma-globulins and liver transaminases served as a criteria of efficacy of the invention. Five patients with hepatitis B and nine with hepatitis C were successfully treated.

Trial 4

Therapeutic use of the invented mixture B in the treatment of chronic allergic rhino-sino-bronchitis Since the chronic allergic rhino-sino bronchitis do not have a common pathogenesis, the diagnosis was based on the clinical picture and the medical history. Before entering the trial following diagnostic tests were performed:

(1) Precise medical history of allergies, medication and atom (family) history.

(2) Functional tests of the lungs (VK and FEV1)

(3) Blood test, BCS-velocity, electrophoresis (4) Amount and duration of the intake of corticoid preparations The efficacy of the invention was based on the normalization tests found pathological at the baseline evaluation, reduction in the corticoid requirement and freedom of symptoms in the follow up periods of 1–2 years. Fifteen patients were successfully treated. Though the efficacy was observed after the elapse of two weeks, it was of long duration.

Based on the trials presented above, following target group can be evaluated for the treatment with the invention:

(1) Patients infected with DNS-viruses of the herpes family, where herpes infection reactivates periodically with varying clinical appearances, ranging from skin rashes and mucous infects to generalized infection.

(2) Patients with chronic active hepatitis caused by DNS hepatitis B or hepatitis C viruses.

(3) Patients with chronic recurrent allergic rhino-sino-bronchitis.

SUMMARY OF THE INVENTION

The invention concerns a plant-based agent having an antiviral and virustatic and antiallergic effect. Diseases caused by DNA viruses of the herpes family or by DNA hepatitis B or C viruses have hitherto been treated prophylactically with expensive agents (e.g. aciclovir, interferon). Patients suffering from chronic allergic rhino-sino-bronchitis are generally administered corticoids and antihistamines which likewise have serious side effects. The invention is intended to be a risk free, effective and economical alternative for the above diseases. Absinthe and/or resin of mastic and/or delphinium denuderum satisfy the above requirements. The addition of rose petals and/or cardamom seeds and/or borage flowers has a synergistic effect. The invention is suitable for treating diseases caused by type 1,2 and 6 herpes simplex viruses, varicella-zoster viruses, cytomegalovirus, Epstein-Bart virus, DNA hepatitis B or C viruses (chronically active hepatitis) and for chronic allergic rhino-sino-bronchitis and also a supportive therapy for HIV infections, pre-carcinoma of the cervix and after organ transplantation.

I claim:

1. A method of treating a patient infected with DNA virus of the herpes family or DNA hepatitis B or hepatitis C viruses, or suffering from chronic allergic rhino-sino-bronchitis, by administering to the said patient a pharmaceutical composition comprising at least two of the compounds selected from the group consisting of absinthe (artemisia absinthium)

resin of mastic (resin pistacia lenticus)

fruit of delphinium denudatum.

2. The method according to claim 1, wherein the pharmaceutical composition further comprises at least one of the compounds selected from the group consisting of rose buds (flores rosae)

seeds of cardamom (fructus ellettaria cardamomum)

borage flowers (flores onosma brateatum boriginaceae).

3. A pharmaceutical composition for treating a patient infected with DNA virus of the herpes family or DNA hepatitis B or hepatitis C Viruses, or suffering from chronic allergic rhino-sino-bronchitis, said composition comprising at least two of the compounds selected from the group consisting of absinthe resin of mastic, and fruit of delphinium denudatum.

4. A pharmaceutical composition according to claim 3 wherein the composition further comprises at least one of the compounds selected from the group consisting of buds of roses, seeds of cardamom, and borage flowers.

* * * * *